United States Patent [19]

Grandadam

[11] Patent Number: 5,147,869
[45] Date of Patent: Sep. 15, 1992

[54] ZOOTECHNICAL COMPOSITIONS

[75] Inventor: Jean A. Grandadam, Saint-Maur des Fosses, France

[73] Assignee: Roussel Uclaf, Paris, France

[21] Appl. No.: 713,696

[22] Filed: Jun. 11, 1991

Related U.S. Application Data

[63] Continuation of Ser. No. 359,962, Jun. 1, 1989, abandoned, which is a continuation of Ser. No. 131,729, Dec. 11, 1987, Pat. No. 4,900,735.

[51] Int. Cl.$^5$ ................ A61K 31/56; A01N 45/00
[52] U.S. Cl. .................................... 514/170; 514/171
[58] Field of Search ......................... 514/170, 171

[56] References Cited

U.S. PATENT DOCUMENTS 4,900,735  2/1990  Grandadam .................. 514/171

FOREIGN PATENT DOCUMENTS 2269332  11/1975  France .................. 514/170
2428440   2/1980  France .................. 514/171

Primary Examiner—Nathan M. Nutter
Attorney, Agent, or Firm—Bierman & Muserlian

[57] ABSTRACT

A zootechnical association comprising a) a zootechnical composition containing 10 to 1,000 mg of salbutamol and 5 to 50 mg of trenbolone acetate and a method increasing the weight and quality of meat of animals by administration simultaneously, separately or spread out over a period of time.

10 Claims, No Drawings

ZOOTECHNICAL COMPOSITIONS

This application is a continuation of U.S. patent application Ser. No. 359,962 filed Jun. 1, 1989 and now abandoned which is a continuation of U.S. patent application Ser. No. 131,729 filed Dec. 11, 1987, now U.S. Pat. No. 4,900,735 issued Feb. 13, 1990.

STATE OF THE ART

Relevant prior art includes U.S. Pat. Nos. 4,192,870 and 4,585,770 and French Patents No. 2,238,476 and No. 2,230,378.

OBJECTS OF THE INVENTION

It is an object of the invention to provide novel technical compositions of salbutamol and trenbolone acetate and a novel method of increasing the weight and quality of meat of warm-blooded animals.

These and other objects and advantages of the invention will become obvious from the following detailed description.

THE INVENTION

The zootechnical compositions of the invention are comprised of 10 to 1,000 mg of salbutamol and 5 to 50 mg of trenbolone acetate.

Beta adrenergics are well known for use in human medicine and certain beta adrenergics are described as having anabolisant activity in animals such as German Patent No. 3,234,995 and European Patent No. 103,830. Applicants have surprisingly found that particularly interesting results are obtained by the association of salbutamol and trenbolone acetate as the association results in a remarkable increase in the weight and quality of the meat of the animals such as bovines, pigs, sheep and fowl. The effect of the said association is much superior to the effect obtained by administering the same beta adrenergic alone or the same steroid alone.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids such as benzoic acid.

Other preferred associations of the invention are those wherein the beta adrenergic is salbutamol of the formula

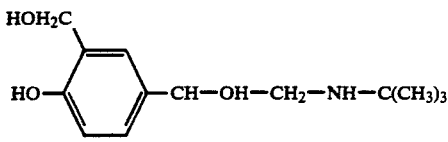

Salbutamol is a known compound and salbutamol or albuterol is α-[tert.butylamino methyl]-4-hydroxy-n-xylene-α,α′diol are known for their activity on beta-2 receptors of bronchial smooth muscles and is sold for the treatment of asthma.

In a preferred embodiment of the invention, the association includes besides, a) a zootechnical composition containing a beat adrenergic of formula I and b) a zootechnical composition containing a steroid of formula A, c) a zootechnical composition containing zeranol or estradiol which components may be administered separately, simultaneously or spread out over a period of time.

Remarkable results are obtained when the product of formula I is (6Rs,trans) 6-isopropylamino-7-hydroxy-4,5,6,7-tetrahydroimidazo[5,4,1-j-k]benzazepin-2-(1H)-one and its non-toxic, pharmaceutically acceptable acid addition salts and the compound of formula A is 17β-acetoxy-Δ$^{4,9,11}$-estratriene-3-one.

Other preferred associations of the invention are a) a zootechnical composition containing salbutamol, b) a zootechnical composition containing trenbolone acetate and c) a zootechnical composition containing either zeranol or estradiol which components may be administered separately, simultaneously or at different periods of time.

Another embodiment of the invention comprises an association of a) zootechnical composition containing a compound of formula I, b) a zootechnical composition containing $b_1$) a compound of formula A and $b_2$) zeranol or estradiol which may be administered simultaneously, separately or spread out over a period of time. Especially preferred are compositions of a) a zootechnical composition containing (6RS, trans) 6-isopropylamino-7-hydroxy-4,5,6,7-tetrahydroimidazo[5,4,1-j-k]benzazepin-2-(1H)-one or its non-toxic, pharmaceutically acceptable acid addition salts and b) a zootechnical composition containing $b_1$) trenbolone acetate and $b_2$) zeranol.

A preferred association of the invention comprises a) a zootechnical composition containing salbutamol and b) a zootechnical composition containing $b_1$) trenbolone acetate and $b_2$) zeranol or estradiol which can be administered separately, simultaneously or spread out over a period of time.

Examples of suitable acids for the formation of the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids such as benzoic acid.

Among the preferred zootechnical compositions are also those which contain salbutamol as the active ingredient.

The associations and zootechnical compositions of the invention increase the weight and improve the quality of the meat of slaughter animals such as bovines, sheep, especially lambs, pigs and calves as well as for fowl.

The beta adrenergics are preferably administered to the animals orally in the form of tablets, granules or powders incorporated into the feed for pigs or calves by the known procedures of such products but they may also be administered parenterally.

The feed mixture will vary depending on the animal species but usually contains cereals, sugars, grains, arachidic and tournsole and soybean press cake, flours of animal origin such a fish flour, amino acids of synthesis, mineral salts, vitamins and antioxidants.

For administration to cattle, the product of formula A as well as zeranol or estradiol which is administered in the form of an implant behind the ear or baleen. It may be implanted 20 days to four months, preferably 1 to 3 months, before slaughter. Zeranol and estradiol can be also administered by injection as a solution or suspension or orally with feed.

The compositions and associations of the invention manifest interesting anabolisant properties, particularly protidic anabolisant properties. They are useful with veterinary medications, especially to increase the general organic resistance to agressions of all sorts, to combat loss of weight, emaciation, general organic problems due to old age and to combat secondary effects of infectious, parasitic and nutritional maladies.

The novel method of improving meat quality and weight in slaughter animals comprises administering to slaughter animals an effective amount of a zootechnical composition or association of the invention as discussed above. The administration may be oral or parenteral and the daily dose will depend on the specific compounds, the method of administration and the animal being treated. The beta adrenergic is usually orally administered at a dose of 10 to 1000 mg/kg or in a zootechnical composition in implant form of 0.5 to 300 mg of the beat adrenergic. Zeranol is usually administered as a zootechnical composition containing 10 to 100 mg of zeranol. Zeranol can be administered as an implant for example. Estradiol is usually administered as a zootechnical composition containing 0.05 to 50 mg of estradiol.

The product of Formula A is usually administered as a zootechnical composition containing 1 to 300 mg of product A.

Particularly interesting associations of the method of the invention are those containing 1 to 100 mg of the beta adrenergic, for example, 5 to 25 mg of the beta adrenergic and implants containing 5 to 50 mg of trenbolone acetate or $17\beta$-acetoxy-$66^{4,9,11}$-estratriene-3-one and 10 to 50 mg of zeranol.

In the following examples there are described several preferred embodiments to illustrate the invention. However, it should be understood that the invention is not intended to be limited to the specific embodiments. The Product $P_1$ in the examples is (6RS, trans) 6-isopropylamino-7-hydroxy-4,5,6,7-tetrahydroimidazo[5,4,1-j-k]benzazepin-2(1H)-one.

EXAMPLE 1

Tablets were prepared containing 5 mg of Product $P_1$ and sufficient excipient of lactose, wheat starch, treated starch, rice starch, talc and magnesium stearate for a final weight of 100 mg.

EXAMPLE 2

Granules were prepared containing 25 mg of Product $P_1$ in each daily dose of granules.

EXAMPLE 3

Associations were prepared consisting of granules containing 25 mg of Product $P_1$ in the daily dose of granules and implant $P_2$ containing 20 mg of trenbolone acetate and 36 mg of zeranol.

EXAMPLE 4

Tablets were prepared containing 5 mg of salbutamol and sufficient excipient of lactose, wheat starch, treated starch, rice starch, talc and magnesium stearate for a final weight of 100 mg.

EXAMPLE 5

Granules were prepared containing 25 mg of salbutamol per daily dose of granules.

EXAMPLE 6

Associations were prepared consisting of a) granules containing 25 mg of salbutamol in the daily dose of granules and b) implants containing 20 mg of trenbolone and implants containing 36 mg of zeranol.

EXAMPLE 7

This test was effected on pigs divided into four groups wherein one group (1) was the control with nothing in the feed, one group (2) receiving 200 mg/kg of Product $P_1$ per day in the feed, one group (3) receiving 250 mg/kg of Product $P_1$ per day in the feed and having an implant of $P_2$ of Example 3 and one group (4) having the implant $P_2$ of Example 3 and nothing in the feed. The product $P_1$ was incorporated into the feed and the implant $P_2$ was placed in the subcutaneous tissue in the rear of the ear. The animals all received the same feed for 90 days and the results are reported in Table I.

TABLE I

| | Groups | | | |
|---|---|---|---|---|
| | (1) | (2) | (3) | (4) |
| No. of pigs | 10 | 10 | 10 | 10 |
| Ave. no. of days of fattening | 28 | 28 | 28 | 28 |
| Ave. weight at implantation in Kg | 82.00 | 81.80 | 81.80 | 81.80 |
| Ave. weight at slaughter in Kg | 103.00 | 103.90 | 107.60 | 103.30 |
| Weight gain in Kg | 21.00 | 22.10 | 25.80 | 21.50 |
| Ave. daily weight gain in Kg | 0.750 | 0.789 | 0.921 | 0.768 |

The results of Table I showed that the treated group had a greater weight gain than the control group but the group (3) of the invention had a very exceptional increase superior to the additive effects caused by the separate administration of Product $P_1$ and implant $P_2$.

EXAMPLE 8

This test was effected on pigs divided into four groups: one group (1) received nothing in the feed, one group (2) received 0.25 mg/kg of salbutamol daily in the feed, one group (3) received 0.25 mg/kg of salbutamol daily in the feed and had an implant $P_2$ of Example 3 and one group (4) received the implant $P_2$ of Example 3 and nothing in the feed. Salbutamol was incorporated into the feed and the implant was placed in the subcutaneious tissue behind the ear. All the animals received the same feed for 90 days and the results are reported in Table II.

TABLE II

| Treatments | Controls (1) | (4) | (3) | (2) |
|---|---|---|---|---|
| Days of treatment before slaughter | | 54 | 54 | 54 |
| No. of pigs. | 9 | 9 | 9 | 9 |

TABLE II-continued

| Treatments | Controls (1) | (4) | (3) | (2) |
|---|---|---|---|---|
| Average weight in Kg on day of treatment | 61.67 | 61.67 | 61.67 | 61.56 |
| Average weight in Kg at end of test | 103.22 | 105.67 | 106.22 | 104.44 |
| Average weight gain in Kg | 41.56 | 44.00 | 44.56 | 42.89 |
| Ave. daily weight gain in Kg | 0.770 | 0.815 | 0.825 | 0.794 |
| Weight of fresh carcasses in Kg | 80.22 | 82.82 | 84.89 | 82.49 |
| Feed consumed in Kg | 130.17 | 129.79 | 129.21 | 130.02 |
| Index of consummation | 3.14 | 2.96 | 2.92 | 3.05 |

Table II shows that the associations of the invention give very good results in increased weight.

EXAMPLE 9

This test was conducted on male calves divided into two groups with group I receiving no additive to the feed and Group II receiving 0.1 mg/kg of live weight of salbutamol. The tests were run three times with a test period of 85 days, a test period of 34 days and a post experimental period of 15 days. The weights were all determined for 15 days and all the animals received a daily ratio of feed throughout the test and the results are reported in Table III.

TABLE III

| Groups | I | II |
|---|---|---|
| No. of calves | 9 | 10 |
| No. of days of fattening | 134 | 134 |
| Ave. weight on day of treatment in Kg | 140.22 | 141.50 |
| Ave. weight in Kg at end of test | 179.00 | 185.40 |
| Ave. weight gain in Kg | 36.88 | 43.90 |
| Ave. daily weight gain in Kg | 1.141 | 1.291 |
| Feed consumed in Kg | 81.90 | 82.00 |

TABLE III-continued

| Groups | I | II |
|---|---|---|
| Consumption index | 2.11 | 1.87 |

EXAMPLE 10

This test was conducted on male and female lambs divided into three groups: group (1) received 0.2 mg/kg of product $P_1$, group (2) received 0.4 mg/kg of product $P_1$ and group (3) was the control group receiving no treatment. Product $P_1$ was incorporated into the feed which was granules in daily quantities and as much hay as they desired. The results shows a clear improvement in weight gain and conformation of the lambs of groups 1 and 2 as compared to control group 3.

Various modifications of the associations and the method of the invention may be made without departing from the spirit or scope thereof and it should be understood that the invention is intended to be limited only as defined in the appended claims.

What I claim is:

1. A zootechnical association comprising a) 10 to 1,000 mg of salbutamol and b) 5 to 50 mg/kg of animal weight of trenbolone acetate in the form of an implant.

2. A method of increasing the weight of pigs comprising administering to pigs a weight increasing effective amount of an association of claim 1.

3. The method of claim 2 wherein the association is incorporated into the pigs feed.

4. A method of increasing the weight of calves comprising administering to calves a weight increasing effective amount of an association of claim 1.

5. The method of claim 4 wherein the association is incorporated into the calves feed.

6. An association of claim 1 also containing 0.05 to 50 mg of estradiol.

7. An association of claim 1 also containing 10 to 100 mg of zeranol.

8. The method of claim 2 wherein the association is administered orally.

9. The method of claim 4 wherein the association is administered orally.

10. A method of increasing the weight of poultry comprising administering to poultry a weight increasing effective amount of an association of claim 1.

* * * * *